(12) United States Patent
Pausch et al.

(10) Patent No.: US 9,364,688 B2
(45) Date of Patent: Jun. 14, 2016

(54) METHOD AND APPARATUS FOR MONITORING THE RANGE OF A PARTICLE BEAM

(71) Applicants: ION BEAM APPLICATIONS, S.A., Lovuain-la-Neuve (BE); Technische Universität Dresden, Dresden (DE); Helmholtz-Zentrum Dresden-Rossendorf e.V., Dresden (DE)

(72) Inventors: Guntram Pausch, Dresden (DE); Christian Golnik, Dresden (DE); Wolfgang Enghardt, Ullersdorf (DE); Guillaume Janssens, Ottignies-Louvain-la-Neuve (BE); Damien Prieels, Court-Saint-Etienne (BE); Julien Smeets, Bouge (BE); Francois Vander Stappen, Brussels (BE)

(73) Assignees: ION BEAM APPLICATIONS, S.A., Louvain-la-Neuve (DE); TECHNISCHE UNIVERSITAT DRESDEN, Dresden (DE); HELMHOLTZ-ZENTRUM DRESDEN-ROSSENDORF E.V., Dresden (DE)

(*) Notice: Subject to any disclaimer, the term of this patent is extended or adjusted under 35 U.S.C. 154(b) by 0 days.

(21) Appl. No.: 14/491,743

(22) Filed: Sep. 19, 2014

(65) Prior Publication Data

US 2015/0087882 A1 Mar. 26, 2015

(30) Foreign Application Priority Data

Sep. 20, 2013 (DE) .......................... 10 2013 218 982
May 26, 2014 (EP) ..................................... 14169907

(51) Int. Cl.
*G21K 1/02* (2006.01)
*A61N 5/10* (2006.01)
*G01T 1/29* (2006.01)
*G01T 1/24* (2006.01)

(52) U.S. Cl.
CPC ................ *A61N 5/1067* (2013.01); *G01T 1/29* (2013.01); *A61N 2005/1052* (2013.01); *A61N 2005/1074* (2013.01); *A61N 2005/1087* (2013.01); *G01T 1/24* (2013.01)

(58) Field of Classification Search
CPC ........ G01T 1/067; G01T 1/24; A61N 5/1067; A61N 2005/1074; A61N 2005/1087
USPC .............................. 250/363.1, 370.07; 600/1
See application file for complete search history.

(56) References Cited

U.S. PATENT DOCUMENTS

2011/0057110 A1    3/2011  Testa et al.
2012/0025076 A1*   2/2012  Kraft ................... A61N 5/1049
                                                  250/307

FOREIGN PATENT DOCUMENTS

WO     WO 2012/152938        11/2012

OTHER PUBLICATIONS

Testa et al. "Dose profile monitoring with carbon ions by means of prompt gamma measurements", Nuclear Instruments and Methods in Physics Research Section B: Beam Interactions with materials and Atoms, Elsevier 2009, 267, pp. 993-996.*
International Search Reported dated Oct. 28, 2014, for PCT/EP2014/070159 (4 pages).
EPO Search Report dated Oct. 10, 2014, for EP 14 16 9907 (3 pages).
* cited by examiner

*Primary Examiner* — David Porta
*Assistant Examiner* — Meenakshi Sahu
(74) *Attorney, Agent, or Firm* — Finnegan, Henderson, Farabow, Garrett & Dunner LLP

(57) ABSTRACT

The invention is related to a method for monitoring a range of a particle beam in a target. The method is using gamma detectors for detecting prompt gammas produced in the target. The time differences between the time of detecting a gamma quantum and a time of emission of a particle or a bunch of particles from the radiation device are determined. A statistical distribution of those time difference is used to deduce information related to the range of the beam. The invention is also related to an apparatus for monitoring a range based on measured time profiles of detected prompt gammas.

20 Claims, 11 Drawing Sheets

METHOD AND APPARATUS FOR MONITORING THE RANGE OF A PARTICLE BEAM

CROSS-REFERENCE TO RELATED PATENT APPLICATIONS

This U.S. patent application claims priority under 35 U.S.C. §119 to German Patent Application No. 102013218982.6, filed Sep. 20, 2013, and European Patent Application No. EP14169907, filed May 26, 2014. The aforementioned applications are incorporated herein by reference in their entirety.

FIELD OF THE INVENTION

The invention relates to a method for monitoring a range or penetration depth of an energetic particle beam in a target by detecting prompt gammas produced when the particle beam penetrates the target. The invention also relates to an apparatus comprising one or more detectors for detecting prompt gammas.

DESCRIPTION OF PRIOR ART

A device for measuring prompt gammas is known from for example reference U.S. Pat. No. 8,481,951B2 or reference WO2012/104416A1 where prompt gammas are measured with a camera that is using one or more collimators. As there exists a known correlation between the emission of prompt gammas and the penetration depth of the particle beam in a target, the penetration depth or the variation of a penetration depth can be deduced by observing prompt gamma data.

However, those prompt gamma cameras are heavy due to the collimators and the detection efficiency is generally poor.

Besides the collimator based prompt gamma detectors, there exist also cameras based on the Compton scattering principle. Both types of cameras are described for example in "Proton Therapy Physics", by H. Paganetti (Editor), CRC Press, Taylor & Francis Group, LLC, 2012, at pages 512-514. However, Compton scattering based prompt gamma cameras, are very complex, expensive and difficult to implement.

Therefore, there is room to develop a method and device that is more robust and less complex than the known prior art prompt gamma cameras.

SUMMARY OF THE INVENTION

The invention is related to a method and apparatus as disclosed in the appended claims.

According to a first aspect of the invention, a method is provided for monitoring the range of a particle beam in a target. The particle beam is delivered by a radiation device. The method of invention comprises the steps of
a) providing a gamma detector configured to detect gamma quanta produced by the particle beam in the target, the detector is configured to generate a detection timing signal which is correlated with a time of detection of a gamma quantum at the gamma detector,
b) providing a reference timing signal which is correlated with a time of emission of a single particle or a particle bunch from said radiation device,
c) detecting gamma quanta with said gamma detector,
d) determining for a number of detected gamma quanta, a time difference between the time of detection of a gamma quantum and a time of emission of the single particle or the particle bunch which has produced the gamma quantum,
e) making a statistical distribution MDIS of the time differences obtained in the previous step,
f) analyzing the statistical distribution MDIS so as to obtain information about the range of the particle beam.

The particle beam typically is a proton beam or an ion beam (such as a carbon ion beam) which is used for particle radiation therapy. The gamma quanta produced in the target by the particle beam are also named prompt gamma quanta.

This method according to the invention uses the characteristic property that when a particle beam penetrates a target, it needs a finite time before it get stopped in the target. If the range of the particle beam is shorter or longer, the corresponding time before the beam is stopped will be shorter or longer. The range (also named penetration depth) of the particle beam can be longer or shorter due to for example a different energy of the particle beam or due to a different composition of the target. The time differences mentioned above in step d) are correlated with the time the particle travels in the target and with the time a gamma quantum needs to travel from the location in the target where it is created towards the detector.

Prompt gamma quanta are produced along the entire trajectory of the particle beam in the target. Therefore the time differences measured will vary according to the location in the target where the prompt gamma is produced. The gamma detector according to the invention is configured to detect gamma quanta emitted from different locations along the trajectory of the particle beam in the target. A statistical distribution MDIS of various measured time differences is then made and this distribution expresses the number of occurrences of a given time difference. Hence, this statistical distribution comprises information about the range of the particle beam. The time a particle beam needs before it is stopped in the target depends on the particle beam energy but it is typically a few nanoseconds. A difference in range in a target of one cm corresponds to a difference in time of about 100 picoseconds.

The gamma detector according to the method and apparatus of the invention is configured to detect gamma quanta produced in a target when the particle beam penetrates the target. As discussed above, those gamma quanta are produced in the target along the entire trajectory of the particle beam in the target. Preferably, the gamma detector is configured to detect gamma quanta produced along the entire trajectory. For example, the gamma detector is configured to detect as well gamma quanta produced at the beginning of the penetration in the target as well as gamma quanta produced at the location where the beam is stopped in the target.

Advantageously, with the method of the invention, range information based on prompt gamma detection is obtained directly from a timing signal. This is in contrast with existing methods using Compton cameras or slit cameras where gamma energy needs to be measured and where cameras are collimated or configured to detect prompt gammas from a specific direction to correlate a detected gamma quanta with the exact location of emission in the target. This spatial resolution is not needed with the present method and apparatus. With the method and apparatus of the invention, a simple inexpensive gamma detector can be used and the gamma detector detects all gamma quanta independently from what location they are emitted.

Preferably, according to the method of invention the step of analyzing the statistical distribution MDIS comprises the additional steps of:
   acquiring a reference distribution REFDIS, said reference distribution REFDIS is corresponding to an expected distribution of time differences,
   comparing said statistical distribution MDIS with the reference distribution REFDES.

In this way, a measured range or range shift, obtained from the statistical distribution, can be compared with an expected range, obtained from the reference distribution defined by for example a treatment planning system.

More preferably, the method according to the invention further comprises the sub-steps of
   i. determining a statistical parameter from the statistical distribution MDIS,
   ii. determining from the reference distribution REFDIS a reference statistical parameter corresponding to the statistical parameter determined in step i),
   iii. comparing the statistical parameter obtained in step i) with the reference statistical parameter obtained in step ii).

Various parameters can be used for the statistical parameter, for example the mean value of the statistical distribution, the centre of gravity of the distribution, the position of the maximum value in the distribution, the width of the distribution. In this way, by comparing a single measured parameter with a planned parameter, a range or range shift can be deduced with high accuracy.

According to a second aspect of the invention, an apparatus is provided to monitor the range of a particle beam in a target as disclosed in the appended claims.

According to a third aspect of the invention, as disclosed in the appended claims, a particle beam system comprising a first gamma detector and a second gamma detector for detecting prompt gammas is provided to determine a particle penetration depth in a target.

According to a fourth aspect of the invention, as disclosed in the appended claims, an alternative method is provided to determine a penetration depth of an energetic particle beam in a target by detecting prompt gammas produced when the energetic particle beam penetrates the target. This alternative method makes use of a first gamma detector and a second gamma detector.

BRIEF DESCRIPTION OF THE FIGURES

These and further aspects of the invention will be explained in greater detail by way of example and with reference to the accompanying drawings in which.

The figures are not drawn to scale. Generally, identical components are denoted by the same reference numerals in the figures.

DETAILED DESCRIPTION OF THE INVENTION

Figure 1:
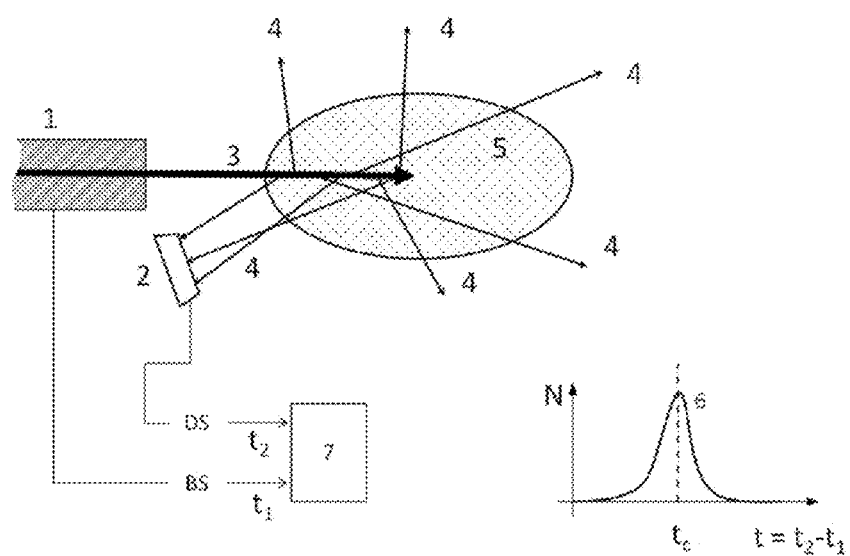
FIG. 1 illustrates a device for monitoring the range of a particle beam according to the invention.

The present invention has been described in terms of specific embodiments, which are illustrative of the invention and not to be construed as limiting. More generally, it will be appreciated by persons skilled in the art that the present invention is not limited by what has been particularly shown and/or described hereinabove. The invention resides in each and every novel characteristic feature and each and every combination of characteristic features.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

The particle beam used for the invention, corresponds to a charged hadron beam, for example a proton beam or a carbon ion beam for use in particle therapy. The energy of the particle beam can vary, depending on the type of particle and on the penetration depth to be reached in the target. The method and apparatus according to the invention can be used for particle therapy in order to determine the penetration depth of a particle or a bunch of particles in a patient. The penetration depth is also named range. The particle beam comprises particles or bunches of particles delivered by a radiation device 1 for radiation therapy.

The method and apparatus of the invention is illustrated in FIG. 1. A radiation device 1 sends a beam 3 to the target 5 and gamma quanta 4 are produced. The target can for example be a target volume in a patient.

A gamma detector 2 for detecting gamma quanta 4 produced by the particle beam in the target 5 is provided. The detected gamma quanta are so-called prompt gammas which are produced when the particle beam interacts with the target. Gamma quanta are produced during the entire trajectory of the particle beam in the target. A portion of the produced prompt gammas are detected by the detector 2. A detected gamma quantum is also named event.

Gamma detectors typically comprise a detector part and electronics for signal shaping. The gamma detector 2 according to the invention is configured to provide for a detected gamma quantum a corresponding detection timing signal DS which is correlated with a time of detection of the gamma quantum at the detector. In other words, the timing signal DS is correlated in time with the arrival of the gamma particle 4 in the gamma detector 2. In this way, for a detected gamma or event, a time stamp or time of detection is associated.

Detectors for measuring gamma quanta such as prompt gammas produced in a target by a particle beam are known. Gamma detectors that are used for this purpose comprise for example scintillator detectors, or Cherenkov detectors or a resistive plate chamber detectors (RPC). A scintillator detector typically comprises a scintillator and a photodetector. The scintillator can be a fast scintillator made of inorganic material or the scintillator can be an organic plastic scintillator or an organic liquid scintillator. Such fast scintillators ensure to have a good timing resolution.

As illustrated in FIG. 1, the gamma detector 2 is preferably located in a location where the gamma quanta are detected in a backward direction when compared with the particle beam direction.

The particle beam has a given time structure depending on the type of radiation device. The time structure reflects when a particle or a bunch of particles are emitted by the radiation device. The particle beam has for example a bunched or pulsed time structure.

According to the method of invention, a reference timing signal is provided which is correlated with a time of emission of a single particle or a particle bunch from the radiation device.

Further, according to the method of invention, for each detected gamma quantum or for a selection of detected gamma quanta in the gamma detector, a time difference is determined between the time of detection of the gamma quantum and a time of emission of the single particle or the particle bunch which has produced the gamma quantum. Those time differences are determined for a multitude of gamma quanta detected.

According to the method of invention, a statistical distribution MDIS 6 of the time differences is made.

The timing signals used in the method and apparatus according to the invention are in the nanosecond range. The time a particle beam need before it is stopped in the target is typically a few nanoseconds (ns), depending on the energy of the beam. A difference in range of one cm corresponds to about a difference of 100 picoseconds.

According to the method and apparatus of the invention, the detection timing signal and the reference timing signal are provided with an uncertainty in time equal or less than 10 ns. Preferably, the detection timing signal and the reference timing signal are provided with an uncertainty in time equal or less than 5 ns and more preferably, those timing signals are provided with an uncertainty in time equal or less than 1 ns.

In an alternative embodiment, the statistical distribution is not based on all gamma quanta detected but only a selected number of gamma quanta. For example, a filter can be placed on the energy of the gamma quanta detected so as to only take the gamma quanta into account that fall within a given energy window. For example, only gamma quanta detected in the energy range between 2 MeV and 8 MeV can be taken into account to make the statistical distribution. In another example, only gamma quanta having an energy between 3 MeV and 5 MeV are taken into account. In a further example, only gamma quanta having an energy between 5 MeV and 7 MeV are taken into account. In another embodiment, the filtering of what events or detected gamma quanta are used to make up the statistical distribution is based on the shape or the amplitude of the detection timing signal.

In a final step according to the method of invention, the statistical distribution MDIS is analyzed so as to obtain information about the range of the particle beam 3.

In a preferred method according to the invention, the step of analyzing the statistical distribution MDIS comprises the additional steps of:
 acquiring a reference distribution REFDIS 61, this reference distribution REFDIS is corresponding to an expected distribution of time differences,
 comparing the statistical distribution MDIS with said the reference distribution REFDES.

As illustrated in FIG. 1, the apparatus of the invention comprises an analyser 7 which comprises a first interface for receiving the detection timing signal DS.

The analyser 7 also comprises a second interface for receiving a reference timing signal BS which is correlated with a time of emission of a single particle or a particle bunch from the radiation device. The reference timing signal is sometimes called Bunch Signal BS. This reference timing signal BS can for example be a signal generated by the RF system of the accelerator of the radiation device. As will be discussed below, in an alternative embodiment the reference timing signal is not obtained from the RF system.

The analyzer 7 comprises a controller that is configured for determining a time difference between a time of detection of a gamma quantum in the gamma detector and a time of emission of the single particle or the particle bunch which has produced the gamma quantum detected. This is illustrated in FIG. 1 where the time $t_1$ of emission of a single particle or a bunch of particles of the radiation device is subtracted from the time $t_2$ corresponding to the time of detection of a gamma quantum in the detector.

The controller is further configured for making a statistical distribution MDIS of time differences resulting from multiple gamma quanta detections in the detector. The time difference $T=t_2-t_1$ is determined for a multiple number of gamma quanta detected in the detector 2. In this way, a statistical time distribution 6 is obtained. This is also illustrated in FIG. 1 where an exemplary distribution 6 is shown on the right side of the figure.

The controller is further configured to analyze the statistical distribution MDIS and derive information about the range of the particle beam. In this way, a statement with respect to the conformity of the performed radiation therapy with respect to a therapy plan can be obtained.

Information about the range is for example a variation of the range when compared to an expected range or a reference range. When for example a deviation between the range and the expected or reference range is observed, a statement of non-conformity can be provided, for example in the form of a warning sign or flag.

According to the apparatus of the invention, preferably, the controller for analyzing comprises an algorithm for comparing the statistical time distribution with an expected or reference statistical time distribution REFDIS.

The expected or reference statistical time distribution REFDIS can for example be a distribution that is previously obtained by measurement under controlled conditions. Alternatively, the expected or reference distribution REFDIS can be obtained using appropriate simulation programs which can be part of a treatment planning system.

More preferably, the controller of the apparatus according to the invention, comprises an algorithm to determine in a first step a statistical parameter from the statistical distribution MDIS, to determine in a second step a reference statistical parameter from the reference distribution REFDIS and in a third step to compare the obtained statistical parameter with the reference statistical parameter.

The statistical parameter determined from the statistical distribution REFDIS can for example be the average or mean value of the distribution, the width of the distribution, the variance of the distribution or any other moment of the distribution.

As an illustration, in FIG. 1, the mean value of the time distribution 6, is indicated and symbolically denoted by $t_c$. Such a statistical parameter is obtained with high accuracy. The value of the statistical parameter changes when the range of the particle beam changes and hence a variation or change of the range is determined with high accuracy.

Preferably, with the apparatus according to the invention the detection timing signal and the reference timing signal are provided with an uncertainty in time equal or less than 10 ns (nanoseconds).

Figure 2:
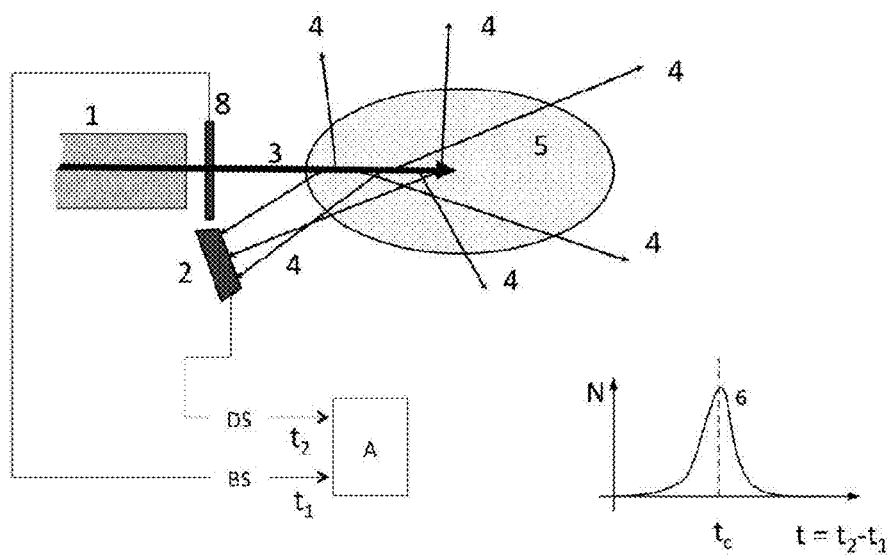
FIG. 2 illustrates an embodiment according to the invention having a particle beam detector.

In FIG. 2, another embodiment of the invention is shown. In this embodiment, the second interface of analyser 7 is connected with a particle detector 8 that is located in the beam. In general, such a detector is placed perpendicular with respect to the beam direction. This detector 8 is a transparent detector in the sense that the beam is transmitted through the particle detector 8. Such a particle detector is also named hodoscope and is known in the art. The particle detector 8 generates at each passage of a single particle, or a particle bunch through the detector, a reference timing signal BS. The generation of the time distribution 6 is then performed in the manner already described above for the embodiment illustrated in FIG. 1 where the radiation device itself (for example through the RF system of the accelerator of the radiation device) is providing a reference timing signal to the second interface of the analyser.

Whether the reference timing signal is produced through the RF system of the radiation device or whether the reference timing signal is produced through the use of a particle detector intercepting the particle beam, this timing signal allows to determine a time of emission of a particle or a bunch of particles out of the radiation device. This time of emission corresponds for example to the time a particle or a bunch of particles passes an imaginary or reference plane perpendicular to the particle beam direction. The imaginary plane can for example be located at the exit of the radiation device. The time $t_1$, indicated on FIG. 1 and FIG. 2 correspond for example to the time a particle or a bunch of particles has passed the imaginary or reference plane.

Figure 3:
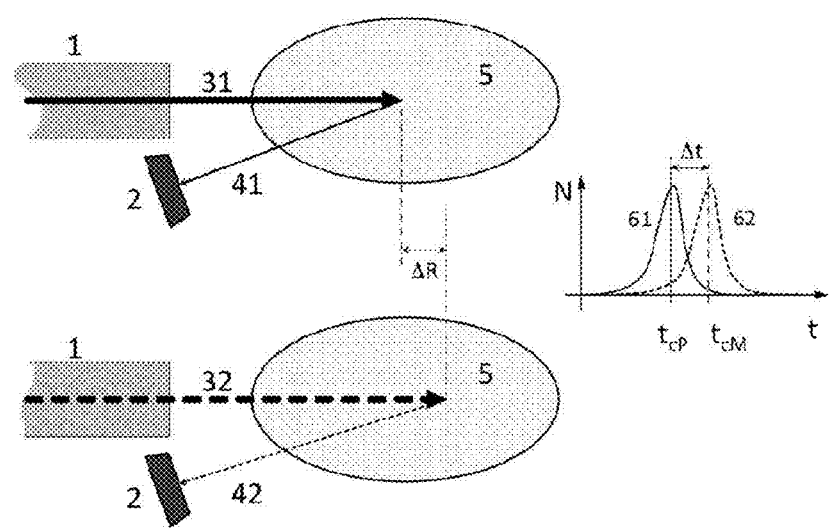
FIG. 3 illustrates a method for determining a range variation.

FIG. 3 further illustrates the use of the apparatus according to the invention. As an example, a situation is assumed where the actual range of the particle beam 32 in the target 5 (lower part of FIG. 3) is greater than the expected or reference range of the particle beam 31 (upper part of FIG. 3). A range shift DR is assumed. The expected or reference range is for example determined by a treatment planning system. As the actual range is larger than the expected or reference range, every particle or bunch of particles of the particle beam 32 need a longer period of time than expected until it is completely stopped in the target. Accordingly, on average, the prompt gamma rays 41,42 emitted are detected in detector 2 at a later moment in time than expected. The mean value $t_{cM}$ of the measured statistical time distribution 62 and the mean value $t_{cP}$ of the planned time distribution 61 (i.e. the expected or reference distribution obtained from a treatment planning system) are shown. The shift in time Dt can be quantified and this shift is a measure of the variation of the range DR.

Alternatively, as discussed above, other statistical parameters of the statistical distribution can be used to compare with an expected or reference statistical parameter. For example, the width of the statistical distribution is also a good parameter to monitor the range. Indeed, the fact that the emission of prompt gamma-radiation starts when the particle beam enters the target and ends when the particle is stopped, the particle beam 32 having a longer range will need a longer time before the beam is stopped and hence the statistical time distribution 62 of the beam with a longer range is wider than the statistical distribution 61 of the beam having a shorter range.

Figure 4:
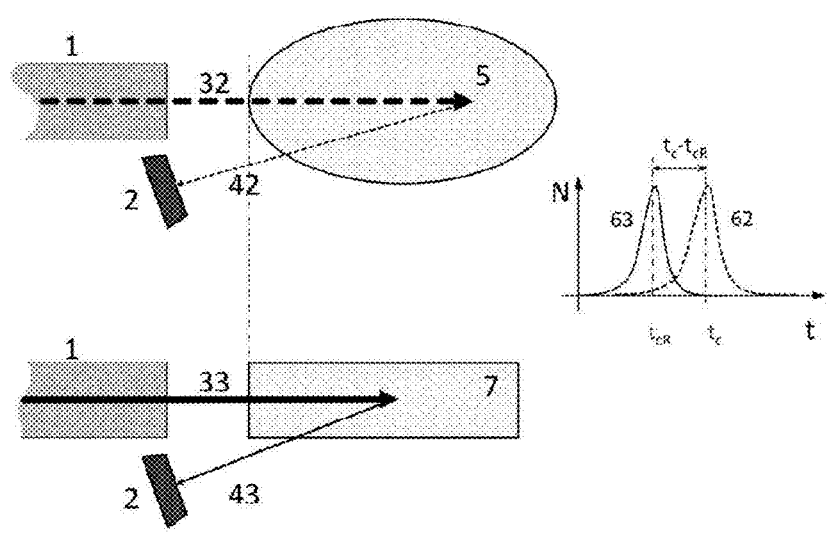
FIG. 4 illustrates a calibration method.

FIG. 4 further illustrates the performance of a calibration of the apparatus of the invention by performing a measurement using a reference target 7. The reference target can for example be a water phantom.

This calibration solves a potential offset problem. Indeed, the detection timing signal and/or the reference timing signal might have offsets. The offsets can for example result from characteristics of the detector 2 used, or from the lengths of signal cables towards the analyzer 7, or from settings of the accelerator of the radiation device.

Dealing with offsets or differences in offsets can be handled by performing the following steps:
in the treatment planning system, both the irradiation of a patient target 5 with a particle beam 32, as well as the irradiation of a reference target 7 with a particle beam 33 are modelled with the same beam parameters. The treatment planning system models the detection of the prompt gammas 42,43 and also models the resulting statistical distributions 62,63 for both cases.
From the statistical distributions of the patient target 5 and the reference target 7 obtained from the treatment planning, a statistical parameter is determined and their difference is determined. For example, as illustrated in FIG. 4, the mean values $t_{cR}$ and $t_c$ are determined from the two distributions. And in a second step, the difference is calculated: $\Delta tP = t_c - t_{cR}$. This delta parameter is named planned delta parameter.
Before irradiation of the patient target 5 with the radiation device, a reference target 7 is irradiated with the radiation device using the same beam parameters as those that were used for the treatment planning model calculation mentioned above. For this reference target 7 a time distribution MDIS 63 is obtained by measurement.
In a further step, the patient target 5 is irradiated with the radiation device and a time distribution MDIS 62 is obtained by measurement.
From the measured time distributions 63 and 62 corresponding to the reference target 7 and the patient target 5, respectively, the statistical parameters $t_{cR}$ and $t_c$ are determined and their difference $DtM = t_c - t_{cR}$ is calculated. This delta parameter is further named measured delta parameter.
Information about the range of the particle beam or information with respect to the conformity of the treatment can be obtained by comparing the planned delta parameter DtP with the measured delta parameter DtM.

Figure 5:
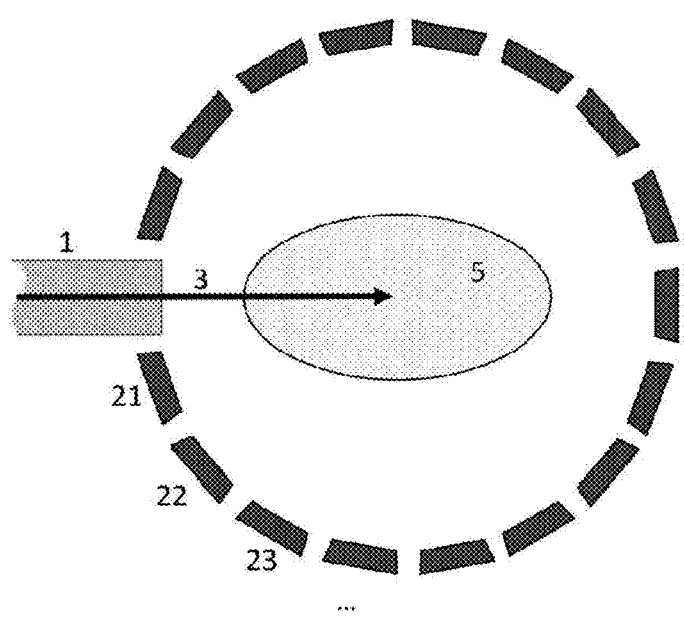
FIG. 5 illustrates an embodiment of the invention using multiple gamma detectors.

FIG. 5 schematically illustrates an embodiment with a plurality of detectors. Using multiple detectors instead of a single detector can have several advantages.

A first advantage is that accuracy of the method can be increased by using multiple detectors 21,22,23. By using one or multiple analyzers 7, a correspondingly larger number of time distributions 6 is obtained and hence a larger number of events or counts is obtained so that the statistical uncertainty of the results is reduced.

A second advantage is that with the use of multiple detectors, the time required to reach a predetermined number of events or counts can be reduced. Such a predetermined number of events or counts is for example imposed by requirements related to the extent of conformity of the treatment with the treatment planning. In other words, the time for taking the decision to interrupt an irradiation based on the time distribution measurements can be shortened.

A third advantage exists for some irradiation facilities that are using accelerators were short but intense beam bunches are delivered. Examples of such irradiation facilities are facilities that comprise a synchrocyclotron or a laser-driven particle accelerator. In such a case, the event rate or count rate per detector can be very large. The count rate per detector can be reduced, by, for example, employing multiple smaller or thinner detectors 2. In this way, the count rate per detector is reduced but by summing the counts of the multiple detectors, still sufficient statistics is obtained to deduce range related information with high accuracy.

Figure 6:
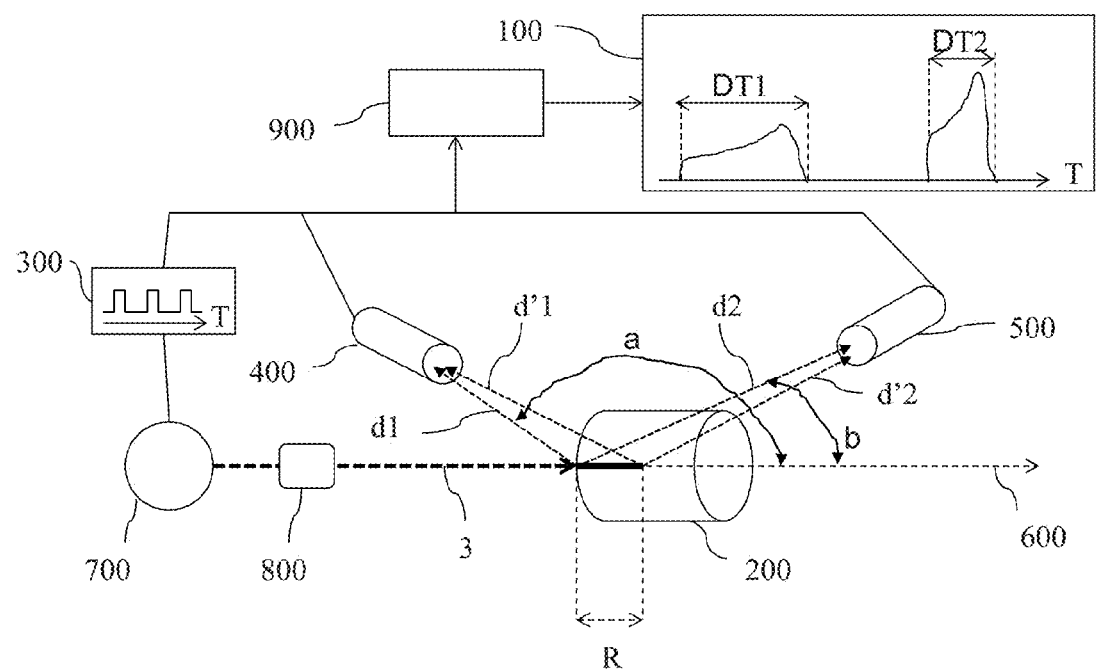
FIG. 6 schematically illustrates an embodiment of the invention using two gamma detectors.

An alternative embodiment according to the invention using at least two gamma detectors is further discussed as illustrated in FIG. 6. According to the invention, a particle beam system for delivering a particle beam 3 to a target 200 is provided. The particle beam system is configured for measuring a penetration depth of a particle beam in a target by measuring prompt gammas emitted when the beam penetrates the target.

This alternative embodiment based on at least two gamma detectors makes use of the same inventive concept as discussed above with respect to for example the embodiments of FIGS. 1 to 5. This common inventive concept is the fact that information of the range or penetration depth of a particle beam in a target is determined based on statistical time distributions obtained by measuring prompt gamma quanta in correlation with the time of emission of a particle or a bunch of particles from the particle beam source or radiation or radiation device.

A particle beam system according to the alternative embodiment of the invention using at least two gamma detectors is schematically illustrated in FIG. 6. The particle beam system according to the invention is comprising a particle beam source 700 for delivering energetic particles or bunches of energetic particles. Those energetic particles or bunches of energetic particles are forming an energetic particle beam 3. The particle beam source can for example comprise a cyclotron, a synchrotron, a synchrocyclotron, a linear accelerator or any type of accelerator accelerating particles for providing an energetic particle beam.

In general, the particle beam source comprises a particle accelerator for delivering protons or ions having an energy larger than 40 MeV per mass unit (mu). For example, for the use of proton beams in particle therapy, the energy of the proton beam can typically vary between 50 MeV and 250 MeV. For heavier beams, such as carbon ion beams, the energy of the beam per mass unit (mu) can typically vary between 80 MeV/mu and 450 MeV/mu.

The particle beam source has a time structure for delivering the particles or bunches of particles. For example when the accelerator is a cyclotron, the particle beam source is delivering particles or bunches of particles having a time structure defined by or correlated with the RF frequency of the RF system of the accelerator. For example, a proton cyclotron can have an RF operating frequency in the range of 100 MHz.

The particle beam system further comprises a timing controller 300 configured for providing a timing reference signal representing the time structure for delivering the energetic particles or bunches of energetic particles. The timing reference signal can be a signal derived from the RF signal of the RF system of the accelerator.

In another embodiment, an additional beam buncher can be used to adapt the time structure for delivering the bunches of particles. The beam buncher can for example optimize the length of the bunch. Preferably, the width of the bunch of the particles is smaller than 200 ps (picoseconds) and more preferably the width of the bunch is equal or smaller than 100 ps (picoseconds).

Alternatively, a detector can be used to intercept the particles of the beam and to generate a timing start signal each time a particle is intercepted. Such a detector is sometimes called a hodoscope. By intercepting particle per particle and associating a start signal to each particle, a timing reference signal representing the time structure for delivering the particles is obtained on a particle per particle base.

The particle beam system according to the invention further comprises beam direction means 800 for directing the particles or bunches of particles in a beam direction 600 pointing the target 200. Such a directing means can for example comprise a beam line to transport the beam and a scanning magnet for delivering the particles or bunches of particles to the target. The delivery means can also comprise a gantry rotatable around the target so as to direct the beam from different rotational angles to the target.

The particle beam system further comprises a first gamma detector 400 configured for detecting prompt gammas from the target and a second gamma detector 500 configured for detecting prompt gammas from the target. The first detector and the second detector are located at a different location with respect to the beam direction 600. The first and second detector are located such that the first and the second detector are oriented for detecting prompt gammas emitted at different angles with respect to the beam direction, as illustrated in FIG. 6.

The particle beam system further comprises a data acquisition system 900 for measuring prompt gammas in synchrony with the timing reference signal so as to obtain a timing profile indicating a number of prompt gammas measured as a function of the time elapsed since the delivery of a particle or a bunch of particles. The first and second detector are coupled to the data acquisition system so as to acquire a first timing profile from the first detector and to acquire a second timing profile from the second detector.

The particle beam system according to the invention comprises a data analyser 100 comprising an algorithm configured for determining from the first timing profile a first time width DT1 and determining from the second timing profile a second time width DT2. The algorithm is further configured for determining a photon travel shift DDP defined as the distance traveled by a photon in the time interval equal to the difference between the first and the second time width, i.e. DDP=(DT2−DT1)*c, whereby c is equal to the speed of light. The algorithm of the data analyser 100 is further configured for determining a penetration depth in the target by correlating the photon travel shift DDP with the difference in detector location between the first and second detector.

Under correlating the photon travel shift DDP with the difference in detector location between the first and second detector is understood that the photon travel shift can be expressed as depending on one hand on the distances the prompt gammas have to travel from the target to the first and second detector and on the other hand depending on a distance R in the target corresponding to maximum depth in the target from where prompt gammas have been emitted. It is well known in the art that this distance R is closely related to the penetration depth of the particle beam in the target as shown for example in FIG. 2 (a) of Gueth et al, Phys. Med. Biol. 58 (2013) pages 4563 to 4577.

Figure 7:
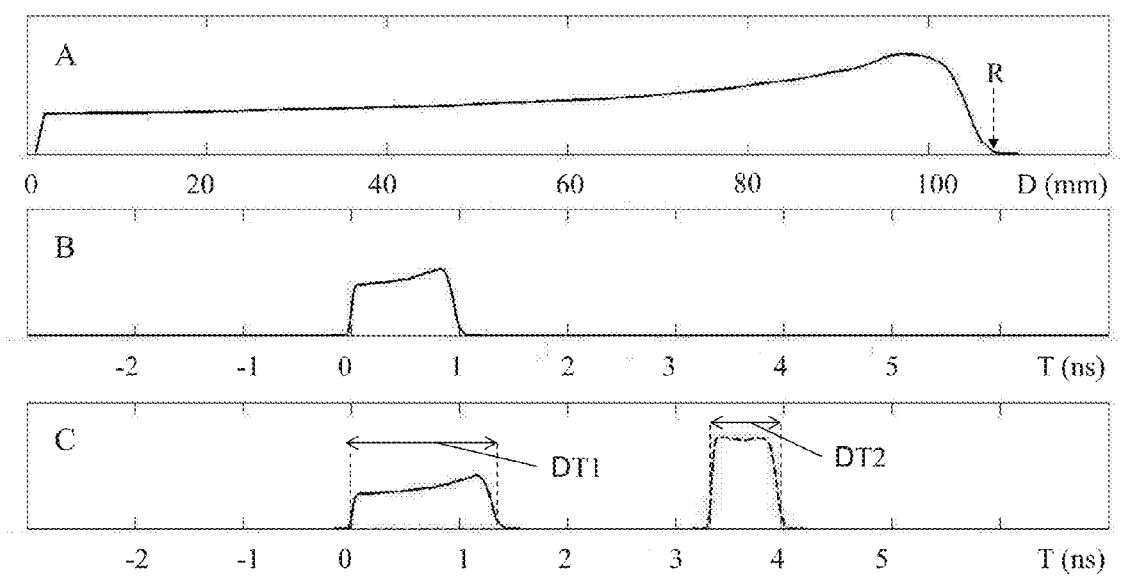
FIG. 7 shows an example of prompt gamma emission and prompt gamma detection profiles.

The invention is further illustrated in FIG. 7 which corresponds to a simulation of a 120 MeV proton beam in a tissue target. In this example, the first detector was located at angle of 180° with respect to the beam direction and the second detector was located at an angle of 0° with respect to the beam direction. The first detector was put on the front side of the target (distance zero) and the second detector was put at a distance of 100 cm from the target entrance. The top panel A shows the relative number of prompt gamma emissions as a function of the depth D in the target, the depth is expressed in mm. The depth R where no further prompt gammas are emitted is indicated on the figure. The middle panel B shows the relative number of prompt gammas emitted as function of time after entering the target. In this example, as can be seen on the middle panel B, prompt gammas are emitted during a time period of about 1 ns (one nanosecond). This time period correspond to the time the particle beam travels in the target until it is stopped when it has lost all its energy in the target.

The lower panel C of FIG. 7 shows the timing profiles as detected with the first detector and the second detector by measuring the prompt gammas in synchrony with the timing reference signal representing the time structure of the particle beam delivered to the target. As can be seen, the widths of the two timing profiles DT2 and DT1 are different. In this example, the two timing profiles in the lower panel C are clearly separated in time due to the large distance of the second detector from the target. In other examples, the second detector can also be put much closer to the target in which case the two timing profiles may overlap.

The correlation between the photon travel shift DDP and the difference in detector location between the first and second detector can be understood from the illustrative geometry shown in FIG. 6. The first time width DT1, measured by the first detector is the difference in time a prompt gamma photon has to travel when either emitted at the entrance of target or emitted at the maximum depth R in the target where prompt gammas are emitted. Following the geometry comprising the distances d1, d2, d'1, d'2 and the two angles a and b illustrated in FIG. 6, the time widths can be expressed as follows:

$$DT1 = d1/c - (Tbeam + d'1/c) \quad (1)$$

$$DT2 = d2/c - (Tbeam + d'2/c) \quad (2)$$

Whereby Tbeam is the time the particle beam travels in the target until it stops when having lost all its energy. This is the penetration depth of the particle beam in the target. As discussed before, the penetration depth of the particle beam is very closely related to the maximum depth position R of emission of prompt gammas.

In the equations (1) and (2), c is the speed of light, d1 is the distance from the first detector to the entrance point, and d2 is the distance from the second detector to the entrance point. The entrance point is defined as the point where the particle beam enters the target. As further illustrated in FIG. 6, d'1 is the distance between the maximum depth R where prompt gammas are emitted and the first detector while d'2 s the distance between the maximum depth R and the second detector.

By taking the difference between DT2 and DT1, one obtains that $$DT2-DT1 = (d2/c) - Tbeam - (d'2/c) - (d1/)c + Tbeam + (d'1/)c$$

Or $$DT2-DT1 = (d2/c) - (d'2/c) - (d1/)c + (d'1/c) \quad (3)$$

In other words, this time difference is independent from the particle beam travel time Tbeam in the target.

As discussed above, a photon travel shift DDP can be defined as $$DDP = (DT2-DT1)*c$$

Or $DDP = d2 - d'2 - d1 + d'1 \quad (4)$

Following standard trigonometric rules one finds that $$DDP = \sqrt{(R*R + d1*d1 - 2*R*d1*\cos(\alpha))} - \sqrt{(R*R + d2*d2 - 2*R*d2*\cos(\beta))} - (d1 - d2) \quad (5)$$

Whereby, as discussed above, R is a distance in the target corresponding to maximum depth in the target from where prompt gammas have been emitted. This is the unknown distance in the target that can be determined with the device and method of the invention. To find R from the above equation number 5, the inventors have used a numerical method to find R.

Preferably, the data analyser 100 according to the invention comprises computing means configured for calculating this distance R in the target by solving the equation number (5) deduced above.

The width DT1 and the width DT2 can be determined in various ways. For example, the timing profiles can be fitted with a curve and the begin and end point of the profile can be deduced. Alternatively, the width can be defined by defining the begin point and the end point of the profile as being a point having a given value with respect to the average peak value, for example defining the begin and end point as being the 5% level points.

Figure 8:
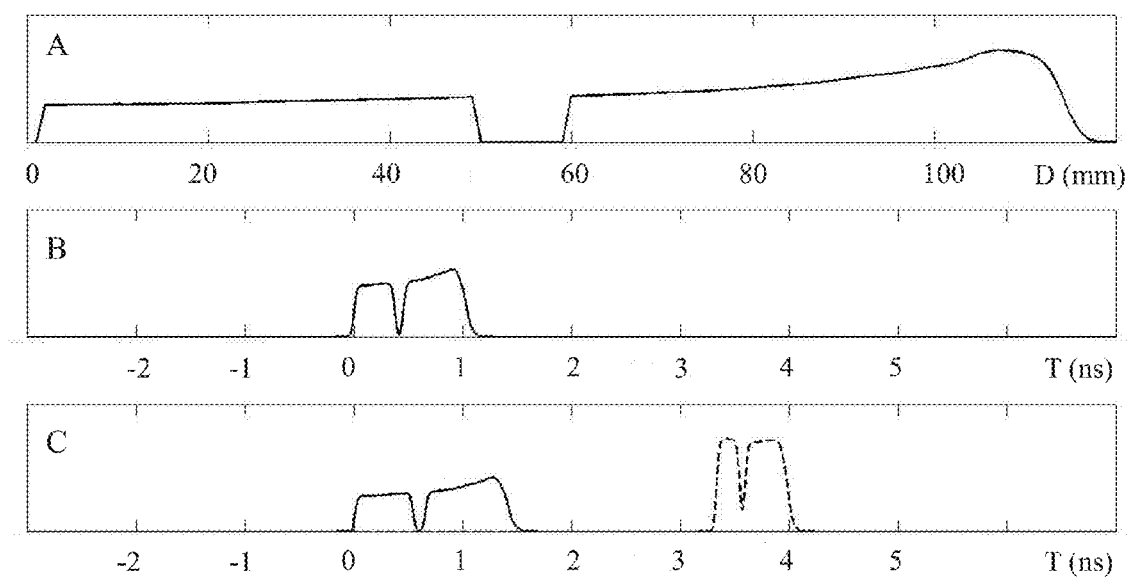
FIG. 8 shows an example of prompt gamma emission and prompt gamma detection profiles whereby a cavity is present in the target.

The inventors have investigated the robustness of the particle beam system according to the invention with respect to inhomogeneities in the target. As an example, the effect of an inhomogeneity is shown in FIG. 8 where an air gap with a thickness 10 mm is located at a depth in the target of 50 mm. In the top panel A, the number of prompt gammas produced as function of the penetration depth in the target are shown. At the location of the air gap, as shown, no prompt gammas are produced. This is then also observed in the middle panel B where the relative number of prompt gammas emitted as function of time after entering the target is plotted. The emission profile in the second panel B is showing a longer emission profile compared with the emission profile of FIG. 7. The third panel C shows that the air gap has also an effect on the shape of the first timing profile and the second timing profile.

Figure 9:
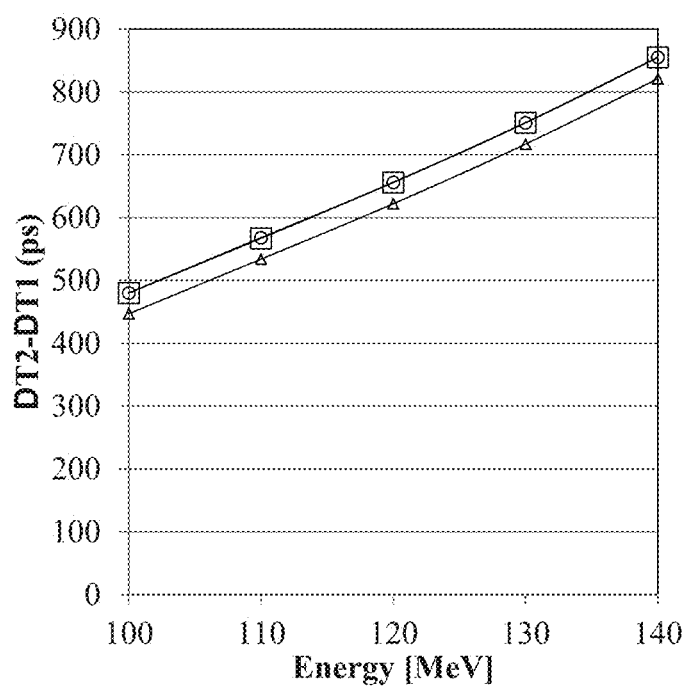
FIG. 9 shows differences in the width DT2−DT1 of timing profiles according to the invention.

It has been found by the inventors that the location of inhomogeneities in the target have no effect on the accuracy for determining the particle beam depth. This is has been examined and is illustrated in FIG. 9 where DT2-DT1 is plotted for proton beams in a plastic target (more specifically a PMMA) having energies between 100 MeV and 140 MeV. Three cases have been evaluated and the results are plotted on the same FIG. 9: 1) circles correspond to a situation where there is a 5 mm cavity located at 1 cm depth in the target, 2) squares correspond to a situation where there is a 5 mm cavity located at 6 cm depth in the target and 3) triangles correspond to a situation where there is no cavity in the target. These results show that not only the 5 mm shift due to the cavity is clearly observed but also that there is no difference for what concerns the location of the cavity so that the particle depth determining method according to the invention shows to be robust.

Figure 10:
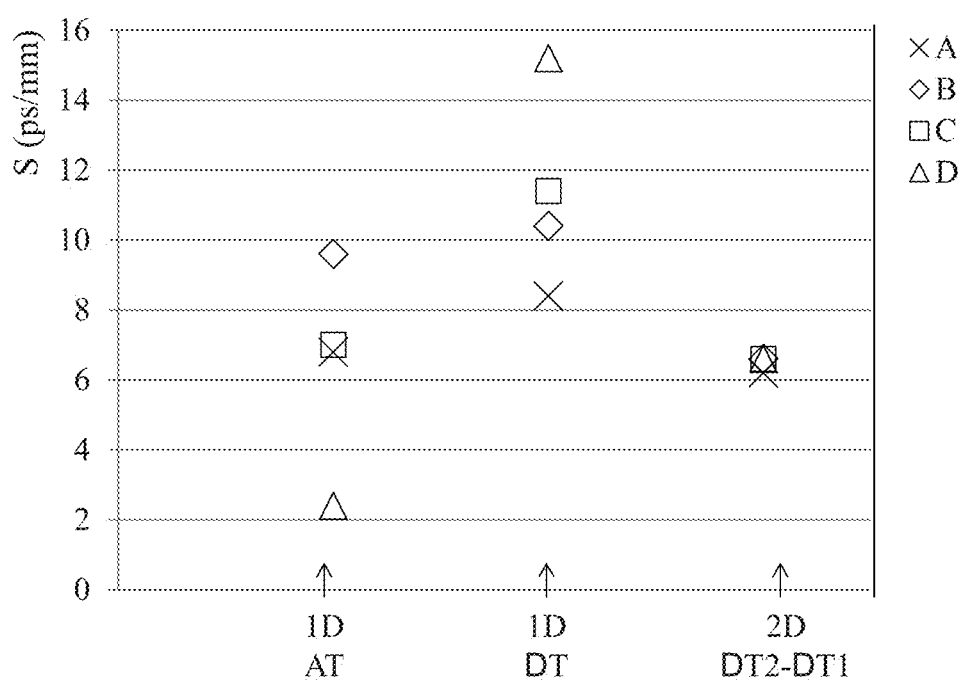
FIG. 10 shows differences in sensitivity between a single detector and a two-detector setup.

The robustness of the particle beam system and the method according to the invention has been further investigated by performing additional simulations. For the exemplary simulation, a beam of 140 MeV of protons was sent on a plastic target (PMMA). The beam was a bunched beam with a bunche duration of 40 ps (picoseconds). The expected particle penetration depth for a homogeneous target having an average density of 1.19 g/cm$^3$ (=reference target) is 12.1 cm. To test the robustness of the method of range verification, four different modifications were made to the target to induce a same 5 mm (millimeter) shift of the penetration depth of the particle beam. The purpose of the test is to demonstrate that the system and method according to the invention can measure such a shift in penetration depth independent of the nature that causes the range shift. Those four modifications made to the target to induce a 5 mm shift in penetration depth, as indicated in FIG. 10, are the following: A) indicated with a cross, is related to target having an overall reduction of the density by 0.05 g/cm$^3$ compared to the reference target, i.e. an average target density of 1.14 g/cm$^3$ instead of the 1.19 g/cm$^3$ for the reference target, B) indicated with a diamond, is related to a target having a cavity of 5 mm located at a depth of 1 cm in the target, C) indicated with a square, is related to a target having a cavity of 5 mm located at a depth of 6 cm in the target, D) indicated with a triangle, is related to a target having a cavity of 5 mm located at a depth of 11 cm in the target. For the four cases A, B, C, D, it is expected that the proton penetration depth shifts with 5 mm compared to the reference target. The purpose of this test was to verify the sensitivity to detect such variations in penetration depth. The sensitivity is defined as the variation of a measured time signal per mm of change of penetration.

The results of the exemplary test simulations are shown in FIG. 10. For this exemplary simulation, a first detector was located at 180° and a second detector at 0° with respect to the beam direction. According to the invention, the values DT2−DT1 were determined for timing profiles obtained with the reference target and with the four modified targets (the cases A, B, C or D as discussed above). The sensitivity S of the detection method according to the invention is obtained by first calculating (DT2−DT1) measured for the four modified targets (A, B, C or D) and subtracting the (DT2−DT1) determined for the reference target and then in a second step dividing this difference in time by the expected penetration shift of 5 mm. This sensitivity S, expressed in ps (picoseconds) per mm (millimeter) is plotted in FIG. 10 on the right side, at the coordinate position labeled "2D DT2−DT1". As shown in this example, the sensitivity using the method according to the invention is about 6.5 ps/mm. This means that one has to measure a time difference of 6.5 ps to detect a variation in penetration depth of one mm. What is important is that the same sensitivity is obtained for the four cases A, B, C, D, i.e. the sensitivity is independent of the nature of what caused the shift in penetration depth (e.g. an overall density change, a cavity in the target, . . . ).

To stress this important advantage of the invention where a particle penetration depth is verified independently of the nature causing a shift in penetration depth, an additional simulation is performed for a system and method that would only use one detector to measure the prompt gammas and hence only obtaining one prompt gamma timing profile. The results are also shown in FIG. 10 where at the coordinate position labeled "1D DT", the results of the sensitivity of a single detector are shown. In this case, the sensitivity is obtained by, in a first step, determining the difference between the width DT measured for a modified target (the case A, B, C or D discussed above) and subtracting the width DT determined for the reference target and then, in a second step, dividing this difference in time by the expected penetration shift of 5 mm. The width DT is defined and determined in the same way as was done for DT1 and DT2, discussed above (equation (1) or (2)). As shown in FIG. 10, for each of the four modified target cases A, B, C and D, four different sensitivity values S are obtained. In other words, when using only one detector for detecting the prompt gammas, the determination of penetration depth requires an exact knowledge of the target structure. For example, if there are cavities in the target one needs to know where they are located in the target.

The reason of this sensitivity variation observed when using only one detector and associated timing profile can be understood from equation (1) or (2), where it is shown that DT depends on Tbeam, the time the particle has to travel in the target. This particle travel time depends on the target structure. As the particle speed decreases when penetrating the target, the travel time will be different when for example a cavity is present in the distal part or the proximal part of the target. With the system and method according to the invention the penetration depth is deduced from a time difference DT2−DT1 independent from Tbeam.

Alternatively, when using only one detector, instead of determining the width DT, one could also determine a average value "AT" of the timing profile. Similarly, the average value AT obtained for the reference target can then be compared with the value obtained for the modified targets (A, B, C, D as discussed above). The results of this approach are also shown in FIG. 10 at the coordinate position labeled "1D AT". As shown, also with this approach the sensitivity for detecting a penetration depth variation is dependent on the target structure.

The timing setup and technology for measuring the two timing profiles with the first and the second detector can adopt technology that is currently used in standard time-of-flight (TOF) measurements used in for example particle beam physics or used for PET time-of-flight measurements (see e.g. Schaart et al. in Phys. Med. Biol. 55 (2010) N179-N189). The first gamma detector and the second gamma detector can be gamma detectors well known in the art such as for example detectors comprising a scintillation crystal and a photomultiplier readout.

With the particle beam system according to the invention, the timing profiles are preferably measured with a timing resolution equal or less than 10 ns (ten nanoseconds). In this way, when accounting for sufficient statistics in the timing profiles (for example, a few 100 to 1000 counts), time differences in the ps (picoseconds) time range can be measured. More preferably, the timing profiles are measured with a timing resolution equal or smaller than 1 ns (one nanoseconds).

Figure 11:
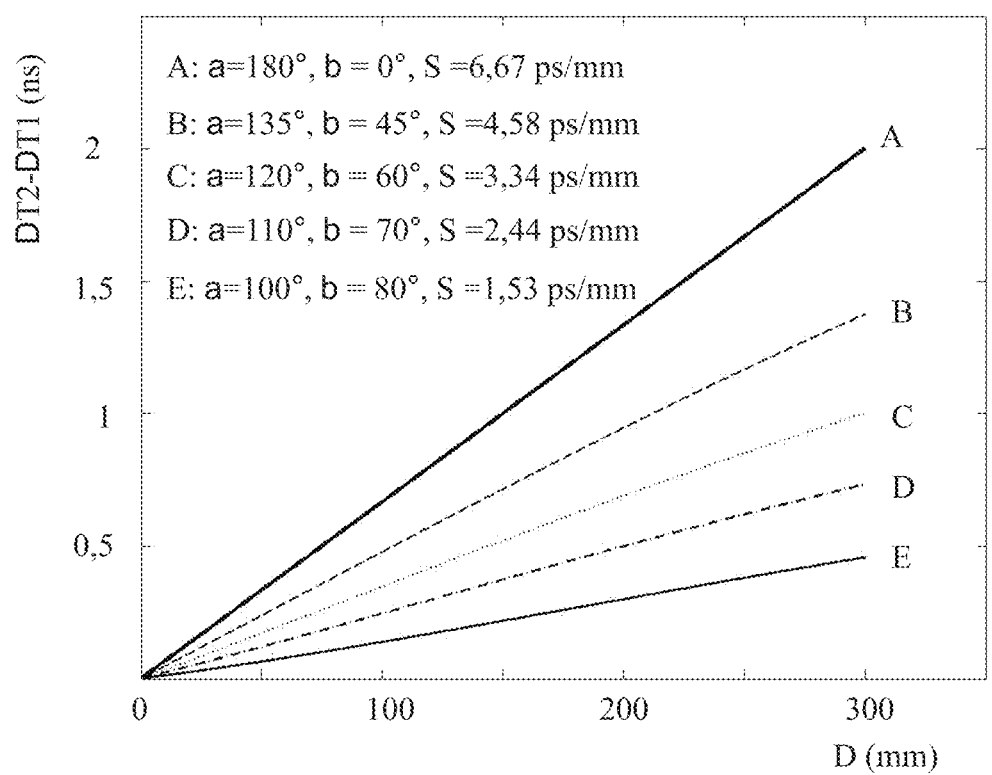
FIG. 11 shows differences in width DT2−DT1 for various setup configurations.

The relative geometry of the first and second detector is further discussed and illustrated in FIG. 11. According to the invention, the first and second detector are positioned at a different angle with respect to the beam direction. The method of the invention can be applied for any position of the two detectors, as long as the two detectors measure prompt gammas emitted from a different direction with respect to the beam direction. In FIG. 11, the time difference DT2−DT1 is plotted as function of the penetration depth D of the beam in the target for different detector setups labelled A, B, C, D, E. Each detector setup is defined by the angles a and b defining the angle between the beam direction and the direction from the target to respectively the first and the second detector. The average sensitivity S for each of the configurations is also plotted on FIG. 11. The highest sensitivity of 6.67 ps/mm is obtained for case A where the two detectors are separated by 180° (degree) and the lowest sensitivity of 1.53 ps/mm is obtained for case E where the two detectors are separated by an angle of 20°.

Preferably, the particle beam system according to the invention has the second gamma detector 500 located with respect to the first gamma detector 400 such that the first and the second detector are detecting prompt gammas emitted at angles that differ by at least 20°. The angles of emission of the prompt gammas are defined with respect to the beam direction.

More preferably, the first gamma detector is configured for detecting prompt gammas emitted at an angle equal or larger than 100° with respect to the beam direction and the second gamma detector is configured for detecting prompt gammas emitted at an angle equal or smaller than 80° with respect to the beam direction.

According to another aspect of the invention, an alternative method is provided to determine a penetration depth of an energetic particle beam in a target by detecting prompt gammas produced when the energetic particle beam penetrates the target. This alternative method makes use of at least two gamma detectors 400,500, for example a first detector 400 and a second detector 500. As also discussed above, a particle beam is formed by particles or a bunch of particles.

As schematically illustrated in FIG. 6, a first gamma detector 400 and a second gamma detector 500 are provided for detecting prompt gammas emitted from the target. In the method according to the invention, the two prompt gamma detectors are located in a different location with respect to the target such that the first and the second detector are configured for detecting prompt gammas emitted at different angles with respect to the beam direction 600.

Further, a timing reference signal representing a time structure of the energetic particle beam is provided. According to the method of the invention, prompt gammas are measured with the first detector in synchrony with the timing reference signal so as to obtain a first timing profile. Similar, with the second detector, prompt gammas are measured with the second detector in synchrony with the timing reference signal so as to obtain a second timing profile.

According to this alternative method of the invention, a first time width DT1 is determined from the first timing profile and a second time width DT2 is determined from the second timing profile. In a next step, a photon travel shift DDP is determined whereby the photon travel shift is defined as the distance traveled by a photon in the time interval equal to the difference between the first and the second time width:

$$DDP=(DT2-DT1)*c$$

whereby c is equal to the speed of light.

Finally, according to the alternative method of the invention, the penetration depth is determined by correlating the photon travel shift DDP with the difference in detector location between the first and second detector.

Preferably, the alternative method of the invention comprises a calculating step for calculating a distance R in the target by solving the equation $$DDP = \sqrt{(R*R + d1*d1 - 2*R*d1*\cos(\alpha)} - \sqrt{(R*R + d2*d2 - 2*R*d2*\cos(\beta)} - (d1-d2)$$

whereby
DDP is the said photon travel shift
d1 is the distance from the first detector to the entrance point, the entrance point being defined as the point where the energetic particle beam enters the target;
d2 is the distance from the second detector to the entrance point;
$\alpha$ is the angle between the beam direction and the direction going from the entrance point towards the first detector;
$\beta$ is the angle between the beam direction and the direction going from the entrance point towards the second detector.

Preferably, in the alternative method according to the invention, the second gamma detector 500 is located with respect to the first detector 400 such that the first and the second detector are detecting prompt gammas emitted at angles with respect to the beam direction 600 that differ by at least 20°.

More preferably, in the alternative method according to the invention, the first gamma detector 400 is located for measuring prompt gammas emitted at an angle equal or larger than 100° with respect to the beam direction and the second gamma detector 500 is located for measuring prompt gammas emitted at an angle equal or smaller than 80° with respect to the beam direction.

The invention claimed is:

1. A method for monitoring the range of a particle beam in a target, said particle beam being delivered by a radiation device, the method comprising the steps of
   a) providing a gamma detector configured to detect gamma quanta produced by said particle beam in said target, said gamma detector is configured to generate a detection timing signal which is correlated with a time of detection of a gamma quantum at said detector,
   b) providing a reference timing signal which is correlated with a time of emission of a single particle or a particle bunch from said radiation device,
   c) detecting gamma quanta with said gamma detector,
   d) determining for a number of detected gamma quanta, a time difference between the time of detection of a gamma quantum and a time of emission of the single particle or the particle bunch which has produced the gamma quantum detected,
   e) making a statistical distribution MDIS of the time differences obtained in the previous step,
   f) analyzing said statistical distribution MDIS so as to obtain information about said range of the particle beam.

2. A method according to claim 1 wherein said step f of analyzing comprises the additional steps of:
   f1 acquiring a reference distribution REFDIS, said reference distribution REFDIS is corresponding to an expected distribution of time differences,
   f2 comparing said statistical distribution MDIS obtained in step e with said reference distribution REFDES obtained in step f1.

3. A method according to claim 2 wherein step f2 further comprises the sub-steps of
   i. determining a statistical parameter from said statistical distribution MDIS,
   ii. determining from said reference distribution REFDIS a reference statistical parameter corresponding to the statistical parameter determined in step i,
   iii. comparing the statistical parameter obtained in step i with the reference statistical parameter obtained in step ii.

4. A method according to claim 3 wherein said reference distribution REFDIS is obtained through a model calculation or the reference distribution REFDIS is obtained from a previously performed measurement.

5. A method according to claim 2 wherein said detection timing signal and said reference timing signal are provided with an uncertainty in time equal or less than 10 ns.

6. An apparatus for monitoring a range of a particle beam in a target, said particle beam comprises particles or bunches of particles delivered by a radiation device for radiation therapy, said apparatus comprising
  a gamma detector for detecting gamma quanta produced by a particle beam in a target, said gamma detector is configured to generate a detection timing signal which is correlated with a time of detection of a gamma quantum at said gamma detector,
  an analyzer comprising
    i. a first interface for receiving as an input said detection timing signal,
    ii. a second interface for receiving as an input a reference timing signal, said reference timing signal being correlated with a time of emission of a single particle or a particle bunch from said radiation device,
    iii. a controller configured for:
      a. determining a time difference between a time of detection of a gamma quantum in the gamma detector and a time of emission of the single particle or the particle bunch which has produced the gamma quantum detected,
      b. making a statistical distribution of time differences MDIS resulting from multiple gamma quanta detections in said detector,
      c. analyzing said statistical distribution MDIS so as to obtain information about said range of the particle beam.

7. An apparatus according to claim 6 wherein said controller is further configured for
  c1. acquiring a reference distribution REFDIS said reference distribution REFDIS corresponding to an expected distribution of time differences,
  c2. comparing said statistical distribution MDIS with said reference distribution REFDIS.

8. An apparatus according to claim 7 wherein comparing the statistical distribution MDIS with the reference distribution REFDIS is performed by
  a) determining a statistical parameter from said statistical distribution MDIS,
  b) determining a reference statistical parameter from said reference distribution REFDIS,
  c) comparing the statistical parameter obtained in step a) with the reference statistical parameter obtained in step b).

9. An apparatus according to claim 7 wherein said detection timing signal and said reference timing signal are provided with an uncertainty in time equal or less than 10 ns.

10. An apparatus according to claim 6 wherein said gamma detector comprises a scintillator detector or a Cherenkov detector or a resistive plate chamber detector.

11. A particle beam system for delivering energetic particles or bunches of energetic particles to a target comprising
  a particle beam source for delivering energetic particles or bunches of energetic particles;
  beam directing means for directing the energetic particles or bunches of energetic particles in a beam direction pointing to said target;
  a timing controller configured for providing a timing reference signal representing a time structure for delivering said energetic particles or bunches of energetic particles;
  a first gamma detector configured for detecting prompt gammas emitted from said target;
characterized in that said particle beam system further comprises
  a second gamma detector configured for detecting prompt gammas emitted from said target and located with respect to said first detector such that the first and the second detector are detecting prompt gammas emitted from different angles with respect to said beam direction;
  a data acquisition system for measuring prompt gammas in synchrony with the said timing reference signal so as to obtain a timing profile indicating a number of prompt gammas measured as a function of a time elapsed since the delivery of a particle or a bunch of particles, said first and second detector are coupled to said data acquisition system so as to acquire a first timing profile from the first detector and to acquire a second timing profile from the second detector;
  a data analyser comprising an algorithm configured for
    a. determining from said first timing profile a first time width DT1;
    b. determining from said second timing profile a second time width DT2;
    c. determining a photon travel shift DDP defined as a distance traveled by a photon in the time interval equal to the difference between the first and the second time width:

$$DDP=(DT2-DT1)*c$$

whereby c is equal to the speed of light;
    d. determining a particle beam penetration depth by correlating said photon travel shift DDP with the difference in detector location between the first and second detector.

12. A particle beam system according to claim 11 wherein said data analyser comprises computing means configured for calculating a distance R in the target by solving the equation $$DDP = \sqrt{(R*R + d1*d1 - 2*R*d1*\cos(\alpha)} - \sqrt{(R*R + d2*d2 - 2*R*d2*\cos(\beta)} - (d1 - d2)$$

whereby
DDP is the said photon travel shift;
d1 is the distance from the first detector to the entrance point, the entrance point being defined as the point where the energetic particles or bunches of energetic particles enter the target;
d2 is the distance from the second detector to the entrance point;
α is the angle between the beam direction and the direction going from the entrance point towards the first detector;
β is the angle between the beam direction and the direction going from the entrance point towards the second detector.

13. A particle beam system according to claim 11 wherein said second gamma detector is located with respect to said first gamma detector such that the first and the second detector are detecting prompt gammas emitted at angles with respect to the beam direction that differ by at least 20°.

14. A particle beam system according to claim 11 wherein said first gamma detector is located for measuring prompt gammas emitted at an angle equal or larger than 100° with respect to the beam direction and said second gamma detector is located for measuring prompt gammas emitted at an angle equal or smaller than 80° with respect to the beam direction.

15. A particle beam system according to claim 11 wherein said data acquisition system is configured to measure said timing profiles with a resolution equal or smaller than ten nanoseconds.

16. A particle beam system according to claim 11 wherein said particle beam source is comprising a particle accelerator for delivering protons or ions having an energy larger than 40 MeV per mass unit.

17. A method for verifying a penetration depth of an energetic particle beam in a target by detecting prompt gammas produced when said energetic particle beam penetrates said target, the method comprising the steps of
providing a first gamma detector configured for detecting prompt gammas;
providing a second gamma detector configured for detecting prompt gammas;
locating said first and second detector in a different location with respect to the target such that the first and the second detector are configured for detecting prompt gammas emitted at different angles with respect a direction of the energetic particle beam;
providing a timing reference signal representing a time structure of the energetic particle beam;
measuring prompt gammas emitted from the target with said first detector in synchrony with said timing reference signal so as to obtain a first timing profile;
measuring prompt gammas emitted from the target with said second detector in synchrony with said timing reference signal so as to obtain a second timing profile;
determining from said first timing profile a first time width DT1;
determining from said second timing profile a second time width DT2;
determining a photon travel shift DDP defined as a distance traveled by a photon in the time interval equal to the difference between the first and the second time width:

$DDP=(DT2-DT1)*c$ whereby c is equal to the speed of light;
determining said penetration depth by correlating said photon travel shift DDP with the difference in detector location between the first and second detector.

18. A method according to claim 17 whereby the step of determining said penetration depth comprises a step of calculating a distance R in the target by solving the equation $$DDP = \sqrt{(R*R + d1*d1 - 2*R*d1*\cos(\alpha))} - \sqrt{(R*R + d2*d2 - 2*R*d2*\cos(\beta))} - (d1 - d2)$$

whereby
DDP is the said photon travel shift
d1 is the distance from the first detector to the entrance point, the entrance point being defined as the point where the energetic particle beam enters the target;
d2 is the distance from the second detector to the entrance point;
$\alpha$ is the angle between the beam direction and the direction going from the entrance point towards the first detector;
$\beta$ is the angle between the beam direction and the direction going from the entrance point towards the second detector.

19. A method according to claim 17 wherein said second gamma detector is located with respect to said first detector such that the first and the second detector are detecting prompt gammas emitted at angles with respect to the beam direction that differ by at least 20°.

20. A method according to claim 17 wherein said first gamma detector is located for measuring prompt gammas emitted at an angle equal or larger than 100° with respect to the beam direction and said second gamma detector is located for measuring prompt gammas emitted at an angle equal or smaller than 80° with respect to the beam direction.

* * * * *